United States Patent
Yokoi et al.

(10) Patent No.: US 7,022,066 B2
(45) Date of Patent: Apr. 4, 2006

(54) CAPSULE ENDOSCOPE

(75) Inventors: Takeshi Yokoi, Hino (JP); Akira Hasegawa, Musashino (JP); Shinya Matsumoto, Machida (JP); Takayuki Suzuki, Hachioji (JP); Hidetake Segawa, Hachioji (JP); Hironobu Takizawa, Hachioji (JP)

(73) Assignee: Olympus Corporation, Tokyo (JP)

( * ) Notice: Subject to any disclaimer, the term of this patent is extended or adjusted under 35 U.S.C. 154(b) by 262 days.

(21) Appl. No.: 10/352,110

(22) Filed: Jan. 28, 2003

(65) Prior Publication Data

US 2003/0171649 A1 Sep. 11, 2003

(30) Foreign Application Priority Data

Mar. 8, 2002 (JP) ............................. 2002-064017

(51) Int. Cl.
*A61B 1/05* (2006.01)
(52) U.S. Cl. ...................... 600/109; 600/167; 600/160; 348/65
(58) Field of Classification Search ................ 600/109, 600/160, 167; 348/65, 76, 340, 294
See application file for complete search history.

(56) References Cited

U.S. PATENT DOCUMENTS

| | | | | |
|---|---|---|---|---|
| 4,745,470 A * | 5/1988 | Yabe et al. | ..................... | 348/76 |
| 4,896,217 A * | 1/1990 | Miyazawa et al. | ........... | 348/340 |
| 4,918,521 A * | 4/1990 | Yabe et al. | ..................... | 348/76 |
| 5,050,584 A * | 9/1991 | Matsuura | ..................... | 600/130 |
| 5,228,430 A * | 7/1993 | Sakamoto | .................... | 600/134 |
| 5,749,827 A * | 5/1998 | Minami | ....................... | 600/109 |
| 5,932,875 A * | 8/1999 | Chung et al. | ................ | 250/239 |
| 6,319,196 B1 * | 11/2001 | Minami | ....................... | 600/130 |
| 6,547,721 B1 * | 4/2003 | Higuma et al. | ............. | 600/133 |
| 6,683,298 B1 * | 1/2004 | Hunter et al. | ................ | 250/239 |
| 6,795,120 B1 * | 9/2004 | Takagi et al. | ................ | 348/294 |
| 2001/0050721 A1 * | 12/2001 | Miyake | ........................ | 348/374 |
| 2002/0165592 A1 * | 11/2002 | Glukhovsky et al. | ......... | 607/62 |
| 2003/0137595 A1 * | 7/2003 | Takachi | ........................ | 348/340 |
| 2003/0146998 A1 * | 8/2003 | Doering et al. | ............. | 348/340 |
| 2004/0199061 A1 * | 10/2004 | Glukhovsky | ................. | 600/312 |

FOREIGN PATENT DOCUMENTS

JP 2001-91860 4/2001
WO WO 00/76391 12/2000

* cited by examiner

OTHER PUBLICATIONS

English Abstract and full translation attached.

*Primary Examiner*—John P. Leubecker
(74) *Attorney, Agent, or Firm*—Arnold International; Bruce Y. Arnold

(57) ABSTRACT

A capsule endoscope includes an image sensor that is fixed to a substrate and is covered by a transparent cover member such that a sealed air space is provided between the objective optical system and the image sensor. Also, a capsule endoscope is disclosed that includes a transparent cover member, an image sensor having an imaging area that is covered by the transparent cover member; and an objective optical system which includes at least two lenses. The lens of the objective optical system that is nearest the image side is either integral with, or is adhered to, the transparent cover member. The transparent cover member seals an air space above the imaging area of the image sensor from dust which may be generated during a focusing adjustment of the two lenses. A focusing method adjusts the position of a first lens, in order from the object side, relative to that of a second lens which is nearest the image side.

20 Claims, 9 Drawing Sheets

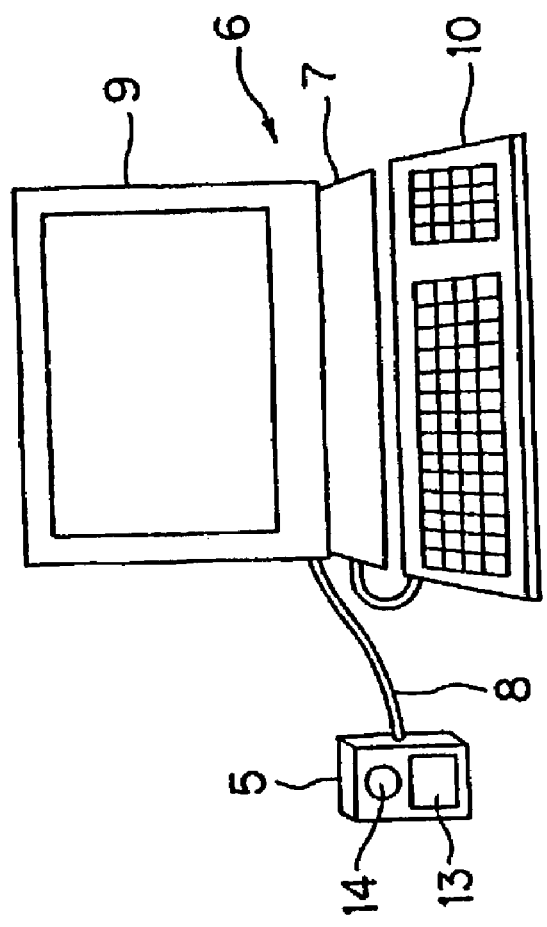
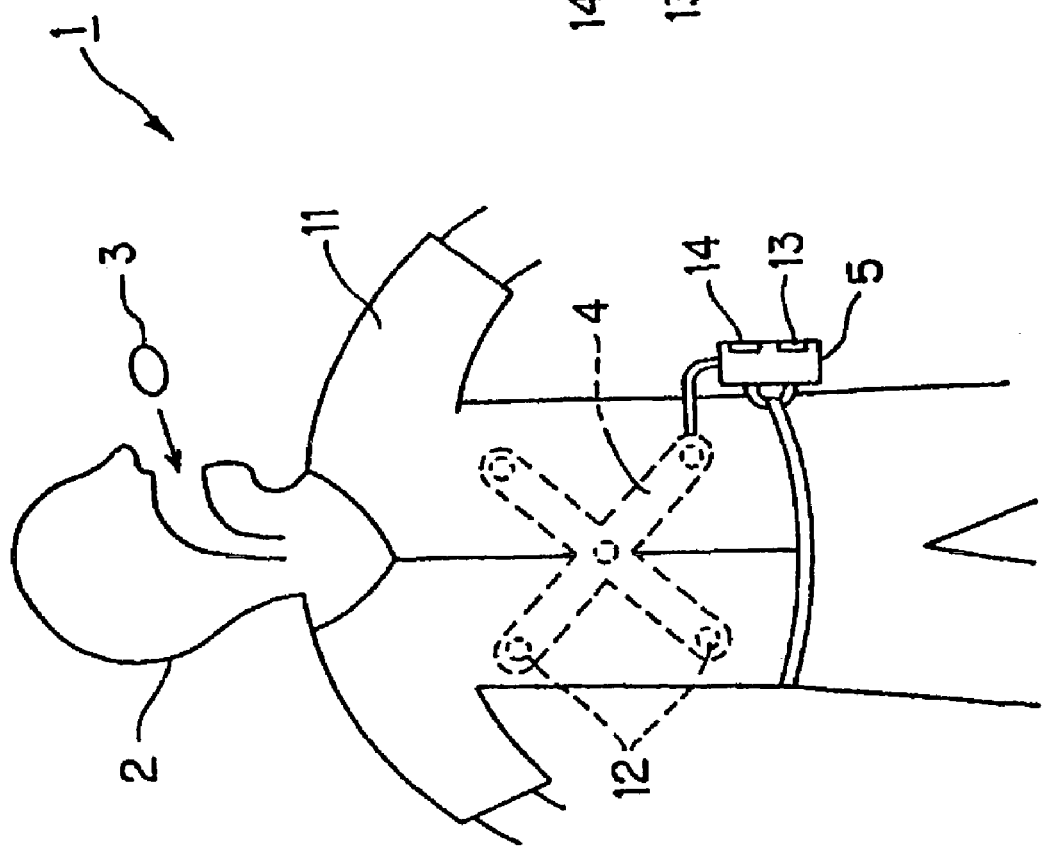

CAPSULE ENDOSCOPE

BACKGROUND OF THE INVENTION

In recent years, endoscopes have been widely used in medical as well as industrial applications. For medical applications, a capsule endoscope has been proposed which greatly reduces the pain associated with obtaining images of internal body parts. Instead of the endoscope including an optical probe having an insertion part, the endoscope is miniaturized and contained within a capsule that is swallowed by a patient. The capsule then radio transmits images as it passes through the body to a receiver located outside the body. One example of such a capsule endoscope is Japanese Laid-Open Patent Application 2001-91860.

In this conventional example, an objective lens and an illumination means formed of light emitting elements which are symmetrically located on opposite sides of the objective lens, are incorporated inside a roughly hemispherical transparent dome. An object is illuminated by the light emitting elements, and reflected light is then imaged onto an image sensor using an objective optical system. Further, the objective lens is fixed relative to the interior of the roughly hemispherical transparent dome as follows. After a barrel for the objective lens is moved with respect to the exposed image sensor so that focusing adjustment is performed, the objective lens is fixed to the lens holding cylinder of the barrel with a fixing screw. Consequently, dust or shaved particles of the lens frame that may be generated upon focusing, may cling to the front surface of the image sensor. Therefore, there has been an instance in which this has prevented a proper image from being obtained. Also, it is possible that such dust or shaved particles may damage the image sensor. Furthermore, where a transparent cover for the purpose of protecting the image sensor has been installed, there has been an instance where dust clings to a surface of the transparent cover and causes a portion of the image to be obscured.

In addition, in the above-mentioned design, the image sensor and the objective lens are positioned via multiple members. Due to the manufacturing and assembly tolerance of each member being finite, this increases the likelihood that an optical parameter of importance, such as angle of view or depth of field, will be incorrect due to the integration of tolerances of many components.

BRIEF SUMMARY OF THE INVENTION

The present invention relates to a capsule endoscope which is to be swallowed for the purpose of obtaining images of the inside of a living body. A first object of the invention is to provide a capsule endoscope that includes a sealed space directly above the image sensor. The sealed space is for the purposes of preventing dust from clinging to the front surface of the capsule endoscope's image sensor even if a focusing adjustment is performed that tends to generate small dust-like particles. A second object of the invention is to provide a simpler focusing adjustment of the optical system by using only a single frame member. A third object of the invention is to provide for an easier assembly of the optical components of the capsule endoscope. A fourth object of the invention is to provide a capsule endoscope having an optical performance which is less sensitive to manufacturing and assembly tolerances of the optical components utilized.

BRIEF DESCRIPTION OF THE DRAWINGS

The present invention will become more fully understood from the detailed description given below and the accompanying drawings, which are given by way of illustration only and thus are not limitative of the present invention, wherein:

FIG. 1(A) shows a capsule endoscope that is about to be swallowed by a person and the associated gear used to receive radio signals transmitted by the capsule endoscope;

FIG. 1(B) is a diagram which illustrates the equipment used to receive and record the images taken by the capsule endoscope;

DETAILED DESCRIPTION

Figure 2:
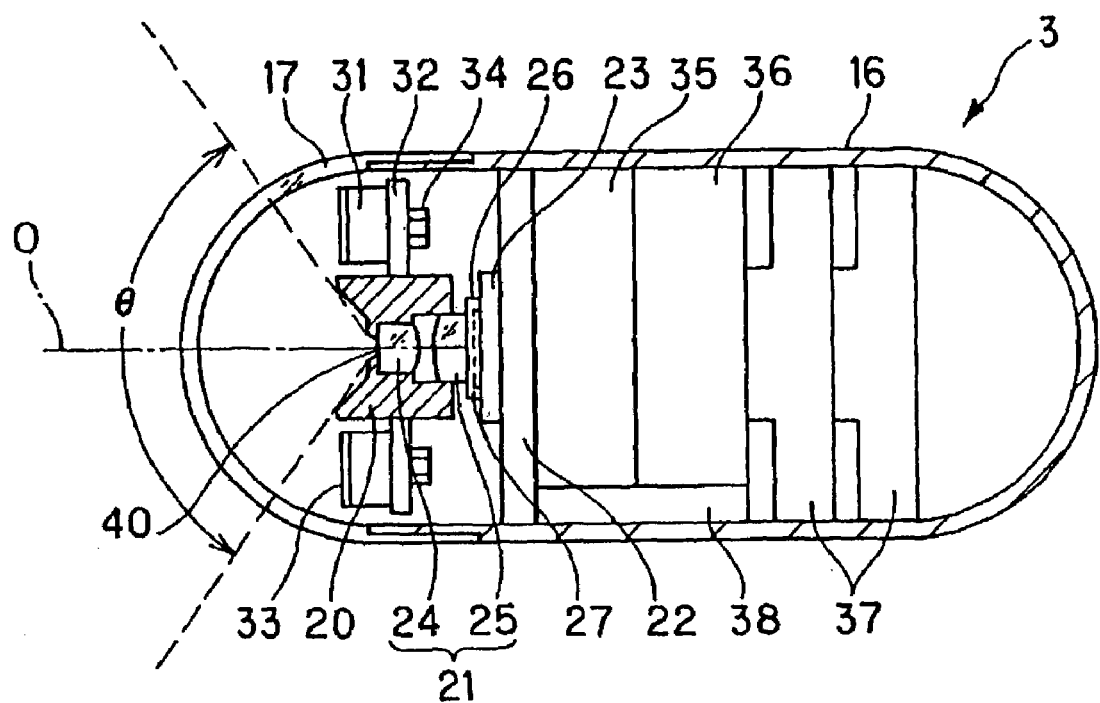
FIG. 2 is a cross-sectional diagram that shows the construction of a capsule endoscope according to Embodiment 1 of the present invention.

In a capsule endoscope where an image sensor, which is fixed to a substrate, and an objective optical system, which is located in front of the said image sensor, are incorporated in an airtight capsule, a space is maintained between the surface of an imaging area and a transparent cover member that covers the imaging area, and the transparent cover member is fixed to the image sensor or to a substrate at the periphery of the imaging area. This design is to prevent dust from clinging to the detecting surface of the image sensor in the event that dust is generated when focus adjustment of the objective optical system is performed.

Hereinafter, various embodiments, and slight modifications thereto, of the present invention will be discussed with reference to the drawings.

Embodiment 1

Embodiment 1 will be discussed with reference to FIGS. 1(A)–6(B). FIGS. 1(A) and 1(B) illustrate components of a capsule endoscope system for performing endoscopic examination of a living body. The capsule endoscope system 1 includes a capsule endoscope 3, which is to be swallowed and which then transmits electromagnetic waves containing image data that is taken when the capsule endoscope passes naturally through a patient's body. Image signals are transmitted by the capsule endoscope using an antenna unit 4 that is attached to a shirt 11 that is worn by a patient 2. An external unit 5, which receives signals from the antenna unit 4, is applied to the exterior of the patient 2, and functions to save images that are transmitted by the capsule endoscope 3.

As shown in FIG. 1(B), the external unit 5 is detachably connected to a personal computer (hereinafter PC), which comprises a display system 6. In the external unit 5, a hard disk of compact flash memory (R) size having a capacity of, for example 1 giga byte, is provided, in order to initially save the picture data. Images which have accumulated in the external unit 5 can be displayed via a display system 6. The display of image data can occur either during the period the capsule endoscope is within the patient's body, or after it has passed naturally through the patient's body.

In other words, as shown in FIG. 1(B), this external unit 5 is detachably connected to a PC 7, which includes the display system 6, using a communication cable such as a USB cable 8. Pictures that have been saved in the external unit 5 can be downloaded by the PC 7, and these pictures can then be saved to an internal hard disk. Also, various processes for the purpose of displaying the pictures can be performed, and the saved pictures can then be displayed by a display 9. A control panel, such as a keyboard 10 for performing data input/output operations is connected to the PC 7.

For the USB cable 8, any of the communication standards among USB 1.0, USB 1.1 and USB 2 is applicable. Further, in addition to these, serial data communication such as using the standard of IEEE 1394 is also applicable. Of course, a parallel data communication cable can be used instead of using serial data communication.

As shown in FIG. 1(A), in the case of performing endoscopic examination by swallowing the capsule endoscope 3, the patient 2 wears a shield shirt 11 which is electrically conductive so as to provide an electromagnetic shielding function, and the antenna unit 4 where multiple antennas 12 are installed is electrically isolated from the shield shirt and is mounted inside it. The shield shirt 11 is designed to receive image signals using the built-in antenna 4 and to enable the conveyance of image data to the external unit 5 by enabling the antenna unit 4 to be connected to the external unit 5. The external unit 5 may be detachably attached to the patient by using, for example, a belt that is worn by the patient and which passes through a loop or hook of the external unit 5. Further, the external unit 5 may have a box-like configuration that includes, on its front surface, a display unit 13 (such as a liquid crystal monitor) and an operation button 14. The interior of the external unit 5 is equipped with a communication circuit for transmission/reception, a control circuit, a picture data display circuit and a power source.

Figures 3A, 3B:
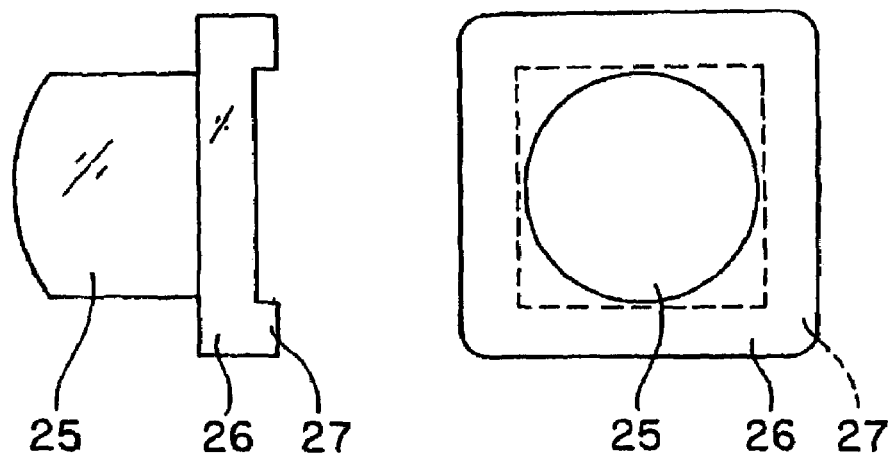
FIGS. 3(A) and 3(B) are side and end views, respectively, which illustrate a transparent cover member that is made integral with a lens element in the construction of a capsule endoscope according to Embodiment 1.

As shown in FIG. 2, in the capsule endoscope 3 of Embodiment 1, a transparent dome 17, which includes a portion shaped as a hemisphere, is connected in a watertight and airtight manner to a cylinder having a rounded back end that forms a rear portion of the capsule endoscope. The following components are contained within the airtight capsule. A single lens frame 20, in a part of the capsule that is near the transparent dome 17, supports an objective optical system 21, with the lens frame having a light-blocking effect. An image sensor 23, such as a CMOS or CCD array, is installed on the front surface of a substrate 22, and the objective optical system 21 forms its image on this same surface. In order from the object side, a first lens 24 is installed within the lens frame 20, and a second lens 25 that is integrally molded to a front surface of a transparent cover member 26 is installed forward of the image sensor 23, as illustrated. Then, the lens frame 20, whose internal diameter slidably engages the exterior diameter of the second lens 25, is moved along the optical axis O in order to perform a focus adjustment, and the lens frame 20 is then fixed in position. Furthermore, glass or synthetic resin is used as the material of the transparent cover member 26 and the integrally molded second lens 25. As shown in FIG. 3(A), the front surface side of the second lens 25 is convex, and the transparent cover member 26 is integrally formed with the rear surface side of this same lens. FIG. 3(B) shows an end view of these structures, as seen looking from the left side in FIG. 3(A).

Figure 4B:
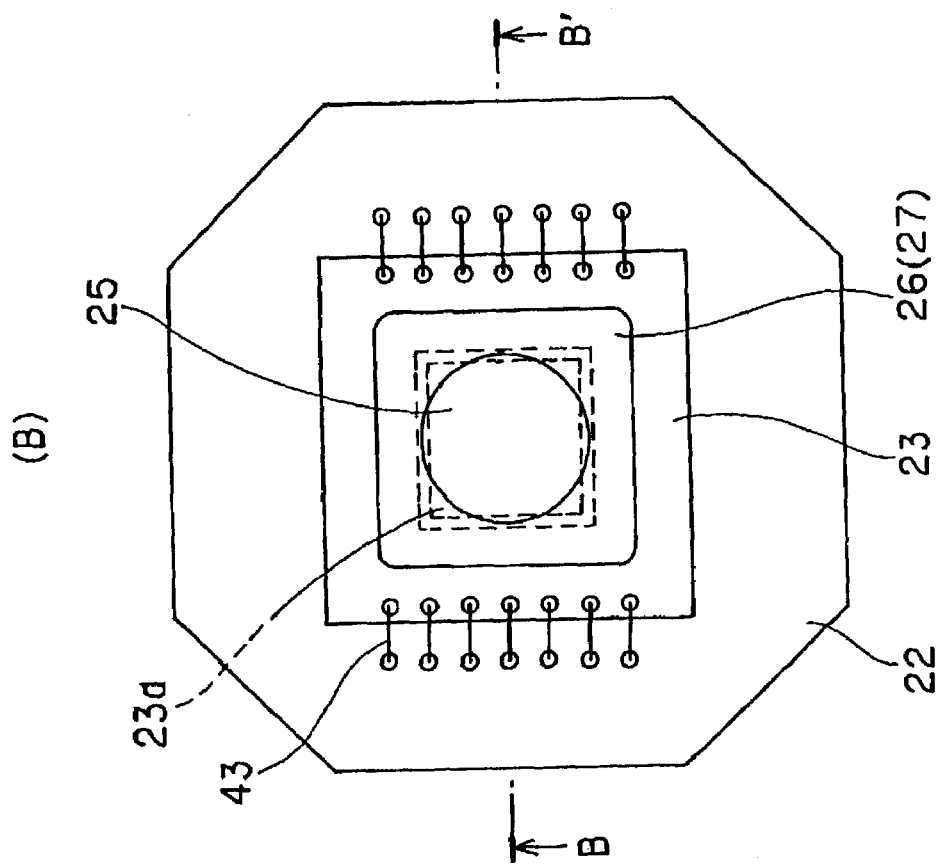
FIGS. 4(A) and 4(B) show an alternative structure that may be formed at the periphery of the imaging part in a first modification to Embodiment 1, with FIG. 4(A) being a cross-sectional diagram taken along line BB' of FIG. 4(B), and with FIG. 4(B) being an end view diagram.
Figure 4A:
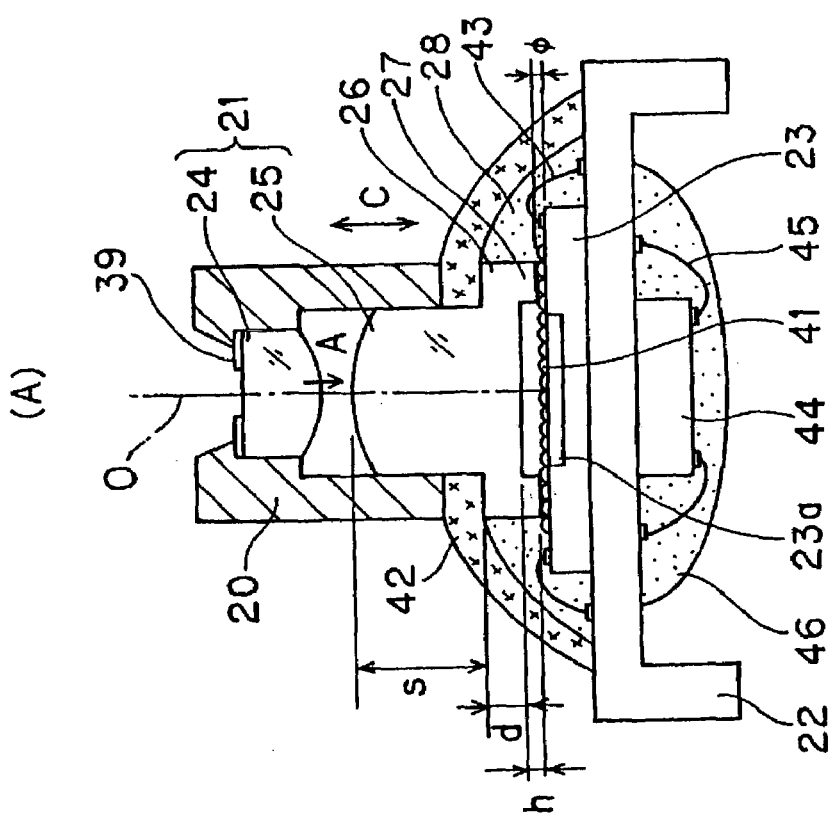

Referring to FIG. 4(A), a raised portion 27 at the periphery of the transparent cover member 26 is sealed to the periphery of the imaging area 23a of image sensor 23 using an adhesive agent 28. In this manner, a space is provided between the transparent cover member 26 and the image sensor 23, and the image sensor 23 is fixed so as to be sealed with the cover member 26. The cover member 26 has a planar rear surface which faces the image sensor, and the raised portion 27 has a square perimeter that surrounds the imaging area 23a.

Referring again to FIG. 2, white LED's 31 which serve as an illumination means are installed on the front surface of substrates 32, and the lens frame 20 supports the substrates 32. This is accomplished by having the lens frame 20 engage the substrates 32 at an opening which is established in the center of the side of the lens frame 20, and the substrates 32 are fixed to the lens frame 20 using an adhesive.

A diffusion plate 33, which functions to diffuse light emitted by the white LED's 31, is installed at the front surface of each LED 31. Further, an LED drive circuit 34 that causes each white LED 31 to flash, is mounted on the back surface of the substrate 32 at each white LED 31.

As shown in FIG. 2, a drive and control circuit 35 is provided. It drives the image sensor 23 via the substrate 22, and is also used to perform signal processing with respect to the output signals while also providing overall control. In addition, a radio communication circuit 36 is provided which transmits picture information that is imaged onto the image sensor 23, and two button-type batteries 37 are provide in series, as illustrated, in order to supply electric power to the radio communication circuit 36. An antenna 38, which is connected to the radio communication circuit 36, is arranged along one side of the drive and control circuit 35 and the radio communication circuit 36. In FIG. 2, the field of view of the objective optical system 21 is indicated by the angle θ, and lies in the range of approximately 90°–140°.

Referring to FIG. 4(A), a brightness diaphragm 39 is arranged on the front surface of the first lens 24, and the center of its entrance pupil is positioned at the center of curvature of both the interior surface and the exterior surface of the transparent dome 17 (FIG. 2). The design is such that white light emitted by the LED's 31, which LED's are arranged around the periphery of the lens frame 20, does not enter into the objective optical system 21 even if the illumination light is reflected by the interior surface of the transparent dome 17.

FIGS. 4(A) and 4(B) show an alternative structure that may be formed at the periphery of the imaging part in a first modification to Embodiment 1, with FIG. 4(A) being a cross-sectional diagram taken along line BB' of FIG. 4(B), and with FIG. 4(B) being an end view diagram. As shown in FIG. 4(A), a two-dimensional micro lens array 41 is installed so as to cover the imaging area 23a of the image sensor 23. The micro lens array 41 enables imaging with an excellent S/N ratio by increasing the quantity of light that would otherwise enter into each pixel of the imaging area 23a. In the present embodiment, raised portion 27 is provided to the cover member 26 that is integrally molded with the second lens 25, and is sealed by a fast-acting adhesive 28 at the periphery of the imaging area 23a. The height h of the raised portion 27 of the cover member 26 is approximately 0.05 mm–0.1 mm. The second lens 25 is installed with its optical axis perpendicular to the surface of the imaging area 23a.

Further, in the present embodiment, a thickness d, which does not include the height of the raised portion 27 in the cover member 26, is established at approximately 0.3 mm–0.5 mm. Furthermore, the space Φ between the image plane and the bottom surface of the raised portion 27 is approximately 20 microns. In addition, the thickness s of the second lens 25 is established at approximately 1 mm–1.5 mm.

In the present embodiment, the lens frame 20 slides along the exterior perimeter of the second lens 25, in the direction of the optical axis O, as indicated by the arrow C in FIG. 4(A) so that a focus adjust is performed. Once the focus adjustment is completed, the lens frame 20 is adhered to the lens 25 using an adhesive 42 that includes a light blocking agent, such as a black color. As explained above, in the present embodiment, before the focusing of the objective optical system 21 is performed, the imaging area 23a is sealed by the cover member 26. As a result, even if dust is generated on the occasion of focusing, the dust is prevented from entering into the imaging area 23a and clinging to the imaging area 23a. In this manner, portions of the imaging area 23a are prevented from being obscured by dust.

As shown in FIGS. 4(A) and 4(B), the electrical components of the image sensor 23 are electrically connected to the substrate 22 at both sides of the imaging area 23a by wire bondings 43. Also, as shown in FIG. 4(A), an electrical component for control or a memory component 44 can be mounted onto the bottom surface of the substrate and can be electrically connected to the substrate 22 by a wire bonding 45, and sealed with a resin 46. As discussed above, a space can be maintained between the imaging area 23a and the rear surface of the cover member that is made integral with the second lens 25, and the imaging area 23a can be sealed by the cover member 26. Therefore, even if dust is generated on the occasion of focusing, the dust can be prevented from entering into the imaging area 23a and clinging to the imaging area 23a; concurrently, this construction can also prevent damage to the imaging area 23a.

Before focusing of the objective optical system 21 is performed, a space is maintained between the imaging area 23a of the image sensor 23 and the raised portion 27 that is provided in the cover member 26, and the imaging area 23a is sealed by the cover member 26 so that dust can be prevented from entering into, and clinging to, the imaging area 23a.

Further, the second lens 25 has a structure wherein the cover member 26 that is integrally molded with the second lens 25 is fixed to the circumference portion of the imaging area 23a of the image sensor 23, so that no lens frame for the purpose of installing the second lens 25 is required. Further, one lens frame 20, within which the first lens 24 is installed, is moved by sliding engagement with the outer periphery of the second lens 25 so as to enable a focusing adjustment to be made for variations in manufacturing tolerance. This enables an excellent quality imaging optical system to be realized so that observation pictures that have an excellent quality can be obtained.

Figure 5:
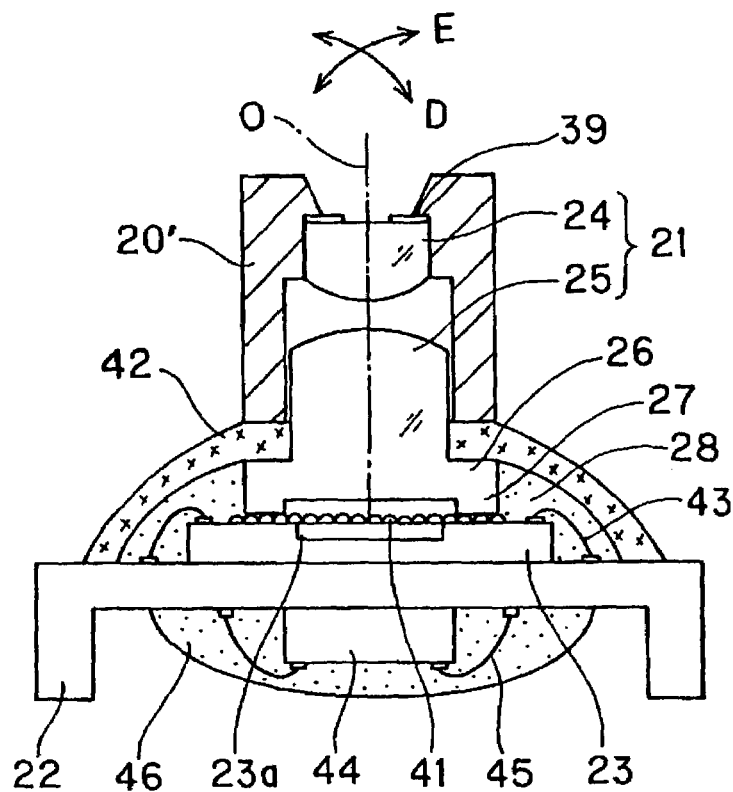
FIG. 5 is a cross-sectional view that shows the structure at the periphery of the imaging part in a second modification to Embodiment 1.

FIG. 5 is a cross-sectional view that shows the structure at the periphery of the imaging part in a second modification to Embodiment 1. In this modified embodiment, the internal diameter of a lens frame 20' is formed slightly larger than the external diameter of the second lens 25. In the case of focusing, the lens frame 20' is supported by a not-shown adjustment jig or a movement guide jig with respect to the second lens 25, which allows for movement along the optical axis O in FIG. 5. In addition, a focusing adjustment may also be performed along the two directions which are indicated by the arrows D and E in FIG. 5 that cross at right angles with the optical axis O. After focus adjustment, the position of the first lens relative to the second lens is fixed as before by applying an adhesive 42 which includes an agent with a light blocking effect. Other constructions are similar to those in the first embodiment. In other words, in this modified embodiment focusing is performed using three-dimensions of movement, so that a more accurate focusing status can be established, and this results in the obtainment of a more excellent image. Further, even if the second lens perimeter has a burr or other small projection resulting from the molding process, there is no problem because the lens frame 20' is not directly adhered to the second lens. This makes it unnecessary to manufacture each component with great accuracy, and enables all components to be produced inexpensively.

Figures 6A, 6B:
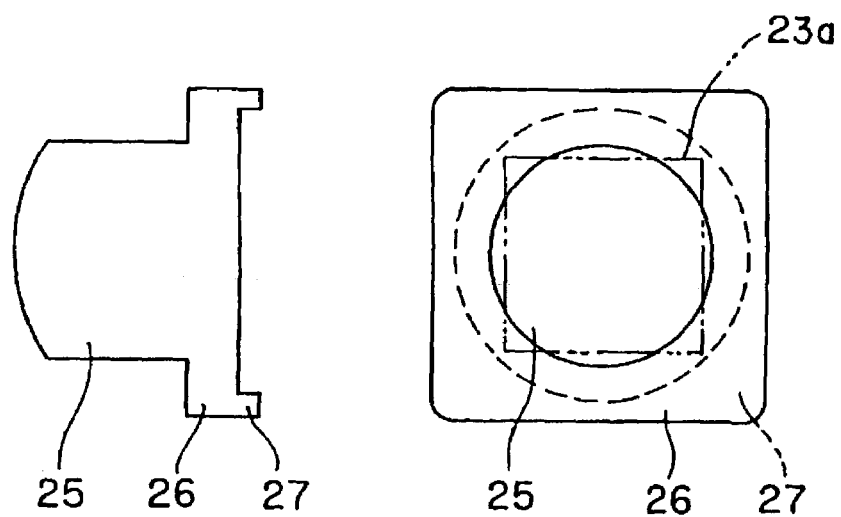
FIGS. 6(A) and 6(B) are side and end views, respectively, which illustrate a transparent cover member that is made integral with a lens element in the construction of a capsule endoscope according to the second modification to Embodiment 1 as illustrated in FIG. 5.

FIGS. 6(A) and 6(B) are side and end views, respectively, which illustrate a transparent cover member that is made integral with a lens element in the construction of a capsule endoscope according the second modification to Embodiment 1 as illustrated in FIG. 5. In FIGS. 3(A) and 3(B), the interior of the raised portion 27 of the cover member 26, which is integral with the second lens 25 and slightly wider than the imaging area 23a, has a square shape. However, in the second modification to Embodiment 1 as shown in FIGS. 6(A) and 6(B), the interior raised portion 27 has a circular shape.

Embodiment 2

Figure 7:
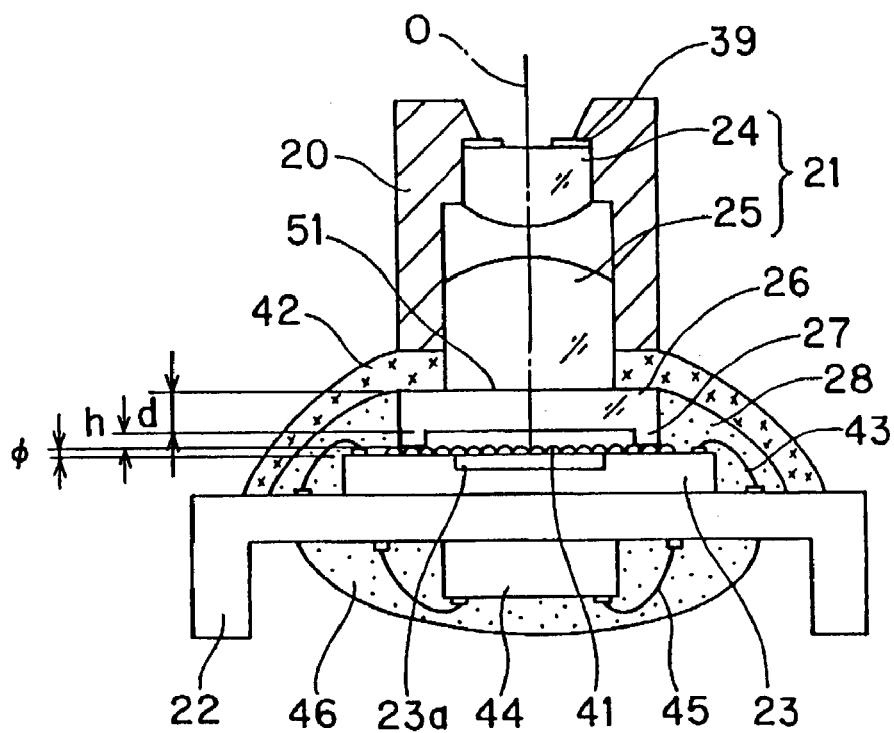
FIG. 7 is a cross-sectional view that shows the structure at the periphery of the imaging part according to Embodiment 2 of the present invention.

The second embodiment of the present invention will be discussed with reference to FIGS. 7 and 8(A) and 8(B). FIG. 7 is a cross-sectional view that shows the structure at the periphery of the imaging part according to Embodiment 2 of the present invention. In Embodiment 1, the cover member 26 was made to be integral with the second lens 25. However, this is not the case in the present embodiment, wherein the second lens 25 and the cover member 26 are made as separate components. Just as in Embodiment 1, the cover member 26 is installed outside of the imaging area 23a of the image sensor 23 using an adhesive 28. Then, the second lens 25 is positioned on the top surface of this cover member 26, and affixed to the cover member 26 using a transparent optical adhesive 51. Next, the lens frame 20 with the first lens 24 installed, is engaged with the second lens 25. After being moved along in the optical axis O direction so that a focusing adjusted can be performed, the lens frame 20 with the first lens installed is fixed into position using an adhesive 42 that includes an agent that has a light blocking effect. In this embodiment, the height h of the raised surface portion 27 is approximately 100 microns, and the thickness d of the transparent cover member 26 is established as about 0.4 mm–0.5 mm. Further, the distance Φ between the image plane and the bottom surface of the raised portion 27 is approximately 20 microns in this embodiment.

Figures 8A, 8B:
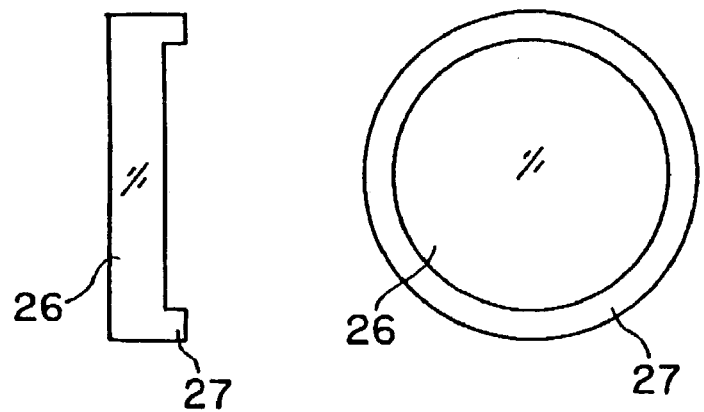
FIGS. 8(A) and 8(B) show side and end views, respectively, of the cover member of Embodiment 2.

FIGS. 8(A) and 8(B) show side and end views, respectively, of the cover member of this embodiment. This cover member 26 has a disk configuration, and the projecting raised portion 27 is formed in the rim. In this case, the planar surface portion inside the raised portion 27 is circular in shape and may be formed, for example, by etching. The other features are similar to those as discussed above for Embodiment 1, and further discussion will therefore be omitted. This embodiment enables the transparent cover member 26 to be formed without using a metal mold, by etching or even scraping, which broadens the materials available for making the cover member 26.

Figure 9:
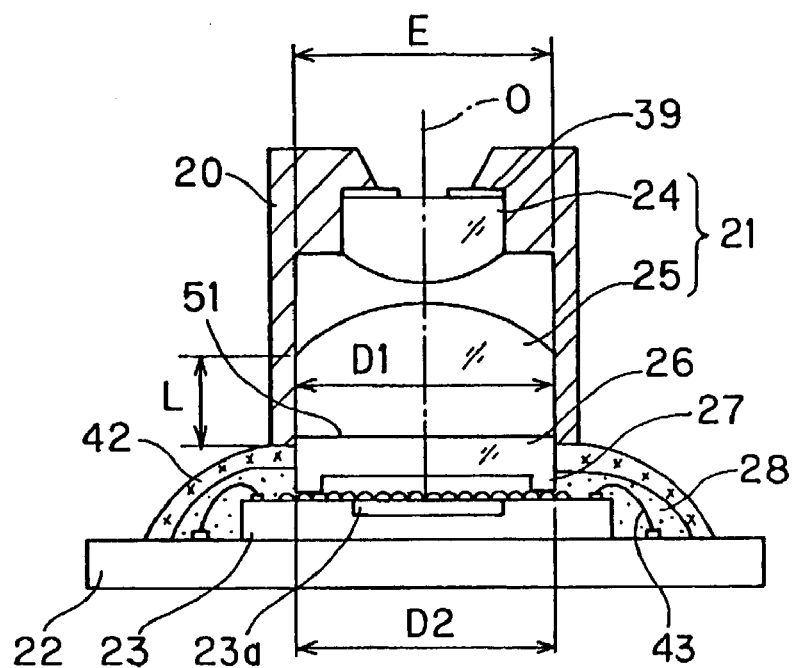
FIG. 9 is a cross-sectional view that shows the structure at the periphery of the imaging part in a first modification to Embodiment 2.

FIG. 9 is a cross-sectional view that shows the structure at the periphery of the imaging part in a first modification to Embodiment 2. In FIG. 9, the external diameter D1 of the second lens 25 is equal to the external diameter D2 of the cover member 26. This enables the external diameters D1 and D2 to both engage with the internal diameter E of the lens frame 20. In other words, the internal diameter E equals the external diameter D1 and also equals the external diameter D2. As shown in FIG. 9, this design enables the lens frame 20 to engage with the cover member 26; therefore the lens frame 20 must be longer. Furthermore, in the present modified embodiment, a disk configuration is adopted for the substrate 22. The other features are similar to those of Embodiment 2 and will not be further discussed. According to the present modified embodiment, the engaging length L can become longer, so that tilting of the first lens 24 and the second lens 25 from the optical axis O direction can be reduced. Further, the strength of the adhesive joint can be enhanced. In addition, efficiency of assembly is improved.

Figure 10:
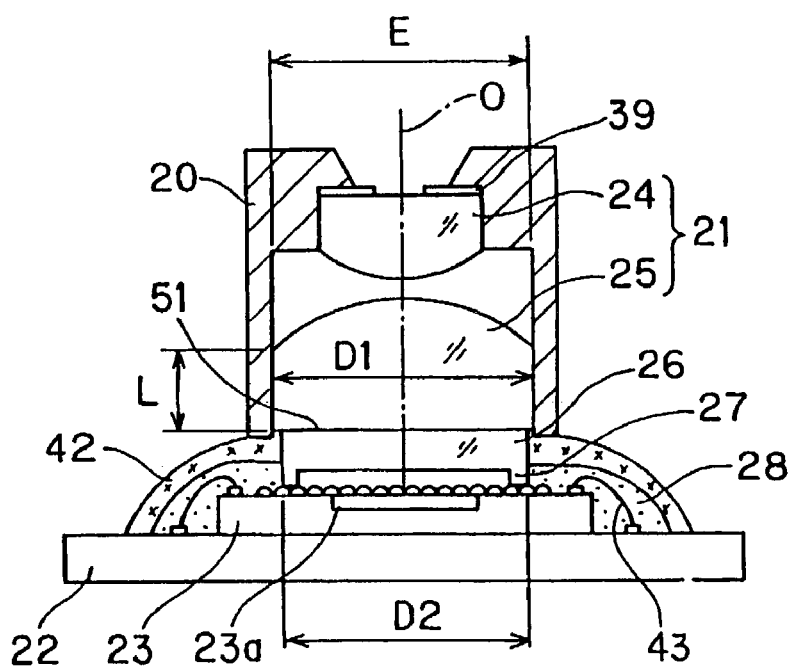
FIG. 10 is a cross-sectional view that shows the structure at the periphery of the imaging part in a second modification to Embodiment 2.

FIG. 10 is a cross-sectional view that shows the structure at the periphery of the imaging part in a second modification to Embodiment 2. In the present modified embodiment, the external diameter D1 of the second lens 25 is larger than the external diameter D2 of the cover member 26. The other features of this embodiment are similar to those of the first modification to Embodiment 2 and will not be further discussed.

Embodiment 3

Figure 11:
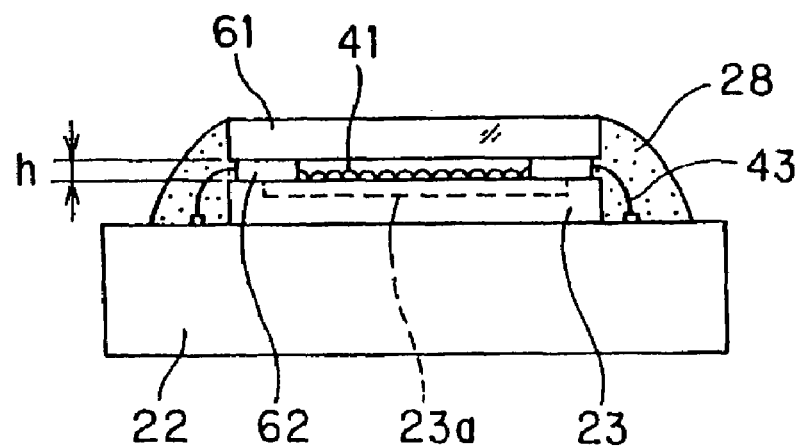
FIG. 11 is a side-sectional view that shows the structure of the imaging part before the objective optical system is installed according to Embodiment 3 of the present invention.
Figure 12:
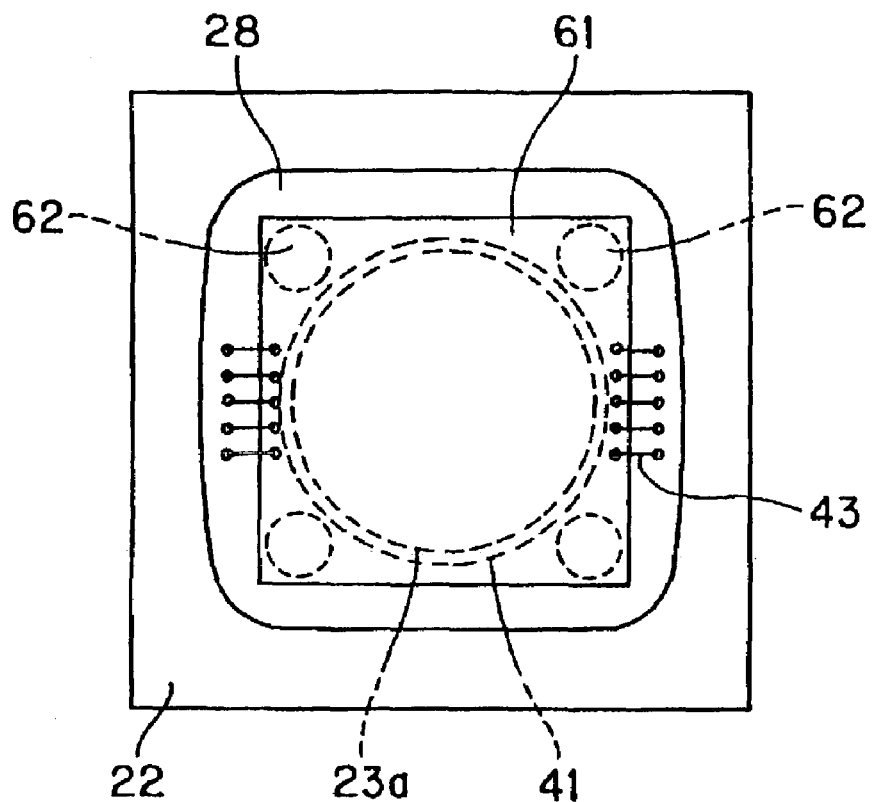
FIG. 12 is a top plan view (i.e., looking from the top in FIG. 11) of the imaging part before the objective optical system is installed according to Embodiment 3.

Embodiment 3 will be discussed with reference to FIGS. 11 and 12. FIG. 11 is a side-sectional view that shows the structure of the imaging part before the objective optical system is installed and FIG. 12 is a top plan view (i.e., looking from the top in FIG. 11) of the imaging part before the objective optical system is installed. In this embodiment, the image sensor 23 has a square, thin plate configuration; however, its imaging area 23a is formed so as to have a circular shape. The micro lens array 41, which covers the imaging area 23a, also has a circular shape. In this embodiment, multiple portions 62 that are integral to the image sensor and positioned at the four corners of the image sensor 23 at the periphery of the imaging area 23a each have a disk configuration and project upwards from the image sensor to a common height. A transparent cover member 61 having, for example, a square plate configuration, is pressed onto and adhered to the portions 62, so that the cover member 61 covers the front surface of the image plane and is parallel to the image plane. An adhesive 28, is used to seal the circumference of the image sensor 23 as well as the wire bonding portion 43. In this embodiment, the height h of the portions 62 is, for example, approximately 50 microns. On the top surface of this cover member 61 is positioned the second lens 25. In addition, the lens frame 20, where the first lens 24 is installed, is engaged with the external diameter of the second lens 25. After a focus adjustment is performed, the lens frame 20 is fixed into position. The other features of this embodiment are similar to that of the second embodiment and will not be further discussed.

Embodiment 4

Figure 13:
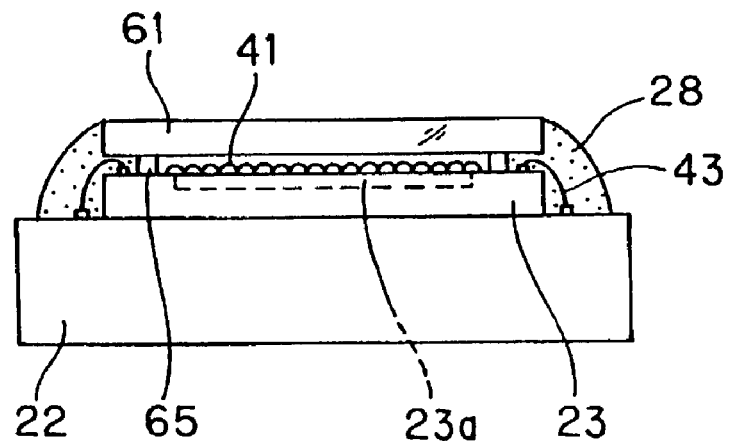
FIG. 13 is a side-sectional view that shows the structure of the imaging part before the objective optical system is installed according to Embodiment 4 of the present invention.
Figure 14:
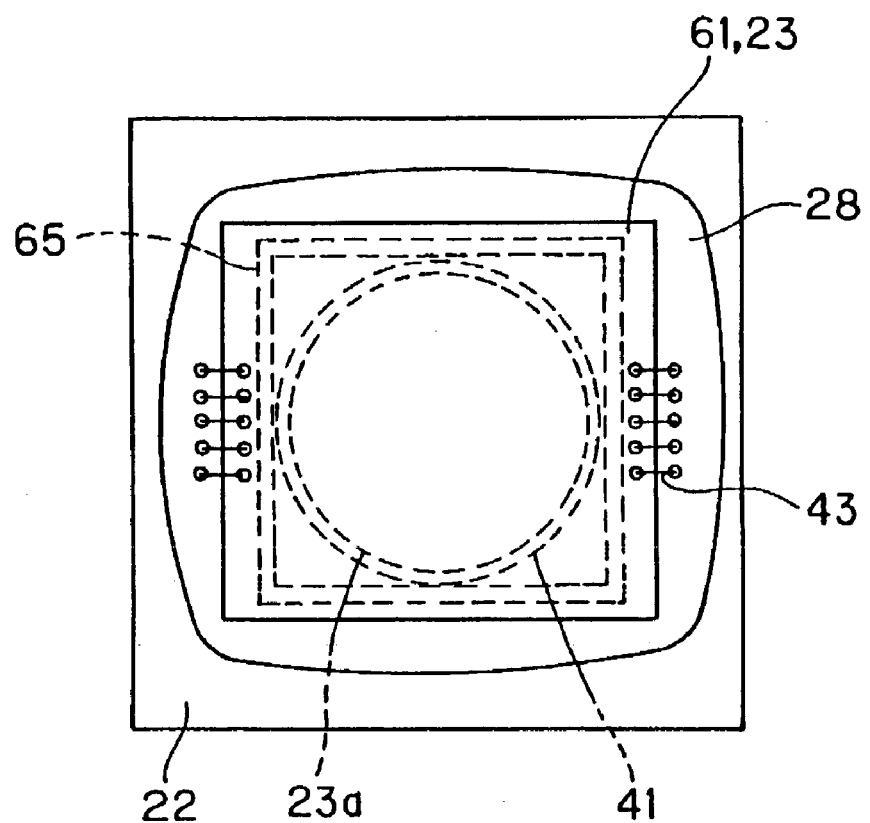
FIG. 14 is a top plan view (i.e., looking from the top in FIG. 13) of the imaging part before the objective optical system is installed according to Embodiment 4.

Embodiment 4 of the present invention will be explained with reference to FIGS. 13 and 14. FIG. 13 is a side-sectional view and FIG. 14 is a top plan view that show the structure of the imaging part of this embodiment before the objective optical system is installed. The cover member 61 is installed to the top surface of the circumference region of the imaging area 23a using a thin plate or spacer 65, such as double-sided tape. The spacer 65 is installed onto the top surface portion of the circumference region of the imaging area 23a of the image sensor 23, and the cover member 61 is then installed above the spacer. An adhesive 28 is then used to sealed these components. In other words, in the present embodiment, the cover member 61 is installed to the image sensor 23 by inserting the spacer member 65, which is separate from the image sensor 23 and the cover member 61. The other features are similar to those of Embodiment 3 and will not be separately discussed.

Embodiment 5

Figure 15:
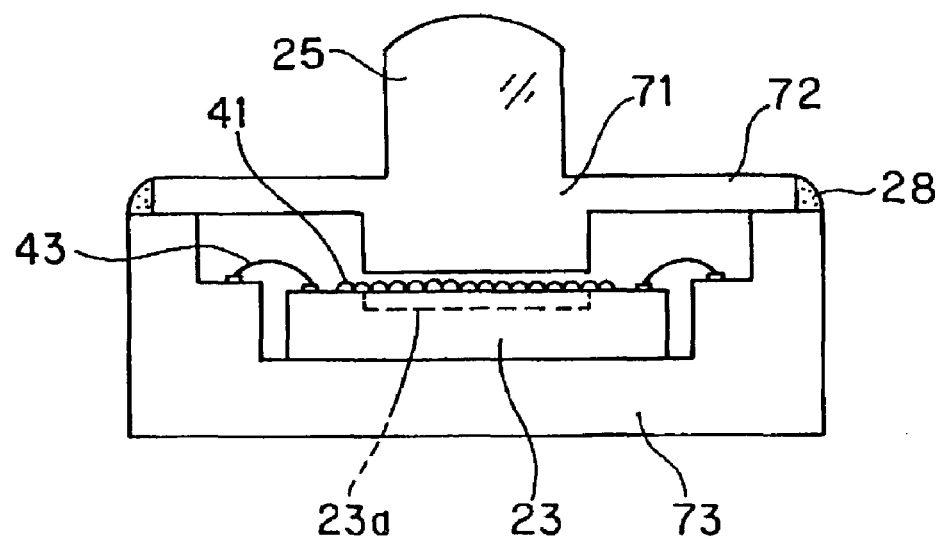
FIG. 15 is a side-sectional view that shows the structure of the imaging part according to Embodiment 5 of the present invention.

Embodiment 5 will be explained with reference to FIG. 15. FIG. 15 is side-sectional view that shows the structure of the imaging part according to this embodiment. A transparent cover member 71 is integrally formed with the second lens 25, and has a portion 72 which extends as a plate outward of the external diameter of the second lens 25. This extended portion 72 abuts against the top surface of a substrate 73 which has been etched or scraped in two steps so as to have two levels, as illustrated, wherein the exterior portion of the substrate is essentially a cylinder which supports the extended portion 72 of the transparent cover member 71. The top surface of the substrate 73 is adhered to the extended portion 72 at various spots and then an adhesive 28 is applied around the circumference of the portion 72 to seal it to the substrate 73. The image sensor 23 is installed onto the lower level, as illustrated, and the micro lens array 41 is applied so as to cover the imaging area 23a. The circuits of the image sensor are electrically connected by wire bondings 43, which are positioned at both sides of the micro lens array 41. The transparent cover member 71 of the present embodiment is designed so that a portion which is opposite the second lens 25 is thicker than the portion 72, and has its bottom surface set slightly above the upper surface of the micro lens array 41. The extended portion 72 of the cover member 71 has its peripheral area fixed to the substrate 73 so that the plane surface of this extended portion 72 becomes parallel to the surface of the imaging area 23a. The lens frame 20, with the first lens installed, is moved for focus adjustment and is then fixedly attached to the second lens 25 as in Embodiment 1. According to the present embodiment, the number of components can be reduced as in Embodiment 1, and thus the production cost and tolerance variations can be similarly reduced.

Embodiment 6

Figure 16:
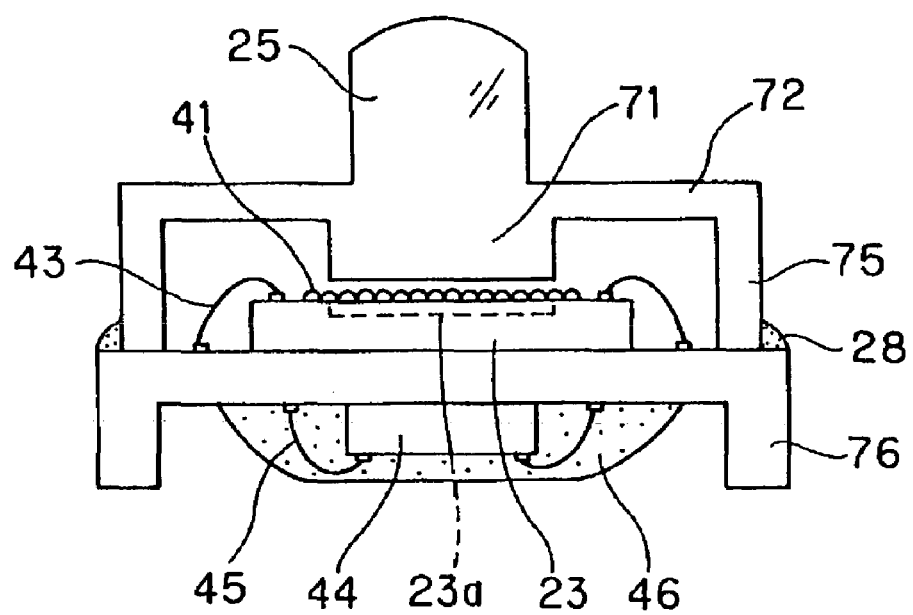
FIG. 16 is a side-sectional view that shows the structure of the imaging part according to Embodiment 6 of the present invention.

Embodiment 6 will be discussed with reference to FIG. 16, which is a side-sectional view that shows the structure of the imaging part according to this embodiment. In this embodiment, a cylinder 75 is formed to extend downward from the periphery of the extended portion 72, as illustrated in FIG. 16, and the bottom surface of this cylinder 75 is adhered at spot locations to the substrate 76. The plane surface of the extended portion 72 is fixed so as to be parallel with the surface of the imaging area 23a, and then an adhesive 28 is applied as illustrated so as to form a sealed interior space in order to protect the imaging area 23a from dust. Further, in the present embodiment, the top surface of the substrate 76 is planar, and the image sensor 23 is installed in the center part, and it is electrically connected to the substrate 76 at each side of the imaging area 23a by wire bondings 43. As is apparent from FIG. 16, the rear surface of the substrate 76 is designed similarly to that of Embodiment 1, i.e., with an electric component or a memory component 44 mounted there which is connected to the substrate 76 by wire bondings 45. As in Embodiment 1, this entire structure is sealed with a resin 46. The present embodiment has similar advantages as discussed above for Embodiment 5.

The invention being thus described, it will be obvious that the same may be varied in many ways. For example, individual features as discussed above for the various disclosed embodiments can be combined so as to form a new embodiment. Such variations are not to be regarded as a departure from the spirit and scope of the invention. Rather, the scope of the invention shall be defined as set forth in the following claims and their legal equivalents. All such modifications as would be obvious to one skilled in the art are intended to be included within the scope of the following claims.

What is claimed is:

1. A capsule endoscope, comprising:
a transparent cover member;
an image sensor that is fixed to a substrate and covered by the transparent cover member, said image sensor detecting images that are formed on a surface within an imaging area, and outside of the imaging area lies a periphery portion;
an objective optical system; and
a transparent dome arranged in front of the objective optical system that is sealed in an airtight and watertight manner to a rear portion of the capsule endoscope; wherein
the transparent cover member is either fixed to the substrate or to said periphery portion such that a space is provided between the surface of the imaging area and the transparent cover member; and
a single lens frame, in a part of the capsule that is near the transparent dome, supports the objective optical system, with the lens frame having a light-blocking effect.

2. The capsule endoscope as set forth in claim 1, wherein the image sensor is an MOS-type image sensor.

3. The capsule endoscope as set forth in claim 1, wherein the image sensor is a CCD-type image sensor.

4. The capsule endoscope as set forth in claim 1, wherein:
at least one protrusion is arranged in the periphery portion outside the imaging area of the image sensor;
the transparent cover member is fixed to said at least one protrusion; and,
surfaces of the imaging area and the transparent cover member are substantially parallel.

5. The capsule endoscope as set forth in claim 4, wherein the at least one protrusion is integrally formed with the image sensor.

6. The capsule endoscope as set forth in claim 4, wherein the at least one protrusion is formed of a member which is separate from the image sensor.

7. The capsule endoscope as set forth in claim 1, wherein the transparent cover member is fixed to the substrate; and,
surfaces of the imaging area and the transparent cover member are substantially parallel.

8. The capsule endoscope as set forth in claim 1, wherein:
at least one protrusion is provided at the periphery of the transparent cover member;
the protrusion is fixed to the surface of said image sensor at multiple spot locations; and,
surfaces of the imaging area and the transparent cover member are substantially parallel.

9. The capsule endoscope as set forth in claim 1, wherein a lens that is located in the objective optical system nearest the image sensor is adhered to the transparent cover member.

10. The capsule endoscope as set forth in claim 1, wherein,
the external diameter of a lens in the objective optical system nearest the image sensor is the same diameter or a larger diameter than the external diameter of the transparent cover member.

11. The capsule endoscope as set forth in claim 1, wherein:
the transparent cover member and a lens in the objective optical system that is nearest the image sensor are integral;
the image sensor side of the transparent cover member includes a planar surface; and
the transparent cover member is fixed to the substrate.

12. The capsule endoscope as set forth in claim 11, wherein the transparent cover member is an integrally molded product made of synthetic resin or glass.

13. A capsule endoscope comprising:
a transparent cover member;
an image sensor having an imaging area that is covered by the transparent cover member; and
an objective optical system which includes at least two lenses; wherein the lens of the objective optical system that is nearest the image side is integral with, or adhered to, the transparent cover member;

the transparent cover member and the lens of the objective optical system nearest the image side are integrally formed as one member; and, the image side of the transparent cover member is planar except for a protruding portion that extends toward the image sensor outside an imaging area of the image sensor.

14. The capsule endoscope as set forth in claim 13, wherein the external diameter of the lens that is located nearest the image side in the objective optical system is the same as, or larger than, the external diameter of the transparent cover member.

15. The capsule endoscope as set forth in claim 13, wherein:

a lens, which is other than the lens of the objective optical system nearest the image side, is fixed to a single frame;

the lens of the objective optical system nearest the image side is engaged with the frame; and, a light shielding means is installed onto the surface of the frame.

16. The capsule endoscope as set forth in claim 13, wherein the objective optical system includes two lenses, each of positive refractive power.

17. The capsule endoscope as set forth in claim 15, wherein an illumination source is fixed in a periphery region of the frame; and, a transparent dome is arranged in front of the illumination source and the objective optical system.

18. A capsule endoscope comprising:

an image sensor;

a transparent cover member that is fixed so as to seal an air space above a surface of the image sensor;

an objective optical system that includes at least two lenses, with the lens nearest the image side being integral with, or adhered to, the transparent cover member;

a lens of the objective optical system, other than the lens nearest the image side, is fixed to a single frame; and, focus adjustment is achieved by adjusting the relative position of a lens nearest the image side relative to the lens of the objective optical system that is fixed to said single frame.

19. A method of providing a focusing adjust to a capsule endoscope, wherein a transparent cover member, which is integrally molded with a lens of an objective optical system that is located nearest the image side, is fixed so as to cover the surface of an image sensor;

a lens, which is other than the lens of the objective optical system that is located nearest the image side, is fixed to a single frame; and the transparent cover member is engaged with said single frame, and focusing adjustment is performed by moving and then fixing said single frame relative to said transparent cover member.

20. A capsule endoscope, comprising:

a transparent cover member;

an image sensor that is fixed to a substrate and covered by the transparent cover member, said image sensor detecting images within an imaging area, and outside of the imaging area lies a periphery portion;

an objective optical system; and a transparent dome arranged in front of the objective optical system; wherein the transparent cover member is either fixed to the substrate or to said periphery portion such that a space is provided between the surface of the imaging area and the transparent cover member; and the transparent dome has a center of curvature, and the position of a pupil of the objective optical system substantially coincides with the center of curvature of the transparent dome.

* * * * *